United States Patent [19]

Narita et al.

[11] Patent Number: 5,166,397

[45] Date of Patent: Nov. 24, 1992

[54] PROCESS FOR PRODUCING OPTICALLY ACTIVE CYCLOBUTYLAMINES

[75] Inventors: Kazuhisa Narita, Ageo; Masashi Nagai; Hideo Sugimura, both of Tokyo; Yukihiro Sagawa, Yono; Akira Shiozawa, Oomiya, all of Japan

[73] Assignee: Nippon Kayaku Kabushiki Kaisha, Tokyo, Japan

[21] Appl. No.: 757,312

[22] Filed: Sep. 10, 1991

[30] Foreign Application Priority Data

Sep. 20, 1990 [JP] Japan ................................ 2-248745

[51] Int. Cl.$^5$ .............................................. C07C 69/74
[52] U.S. Cl. .................................. 560/1; 556/413; 560/106; 560/252; 564/303; 564/304
[58] Field of Search ........................... 560/1, 106, 252; 564/303, 304; 556/413

[56] References Cited

U.S. PATENT DOCUMENTS 5,057,535  10/1991  Shiozawa ............................ 514/428

FOREIGN PATENT DOCUMENTS 0358154  3/1990  European Pat. Off. .
0366059  5/1990  European Pat. Off. .

OTHER PUBLICATIONS

Morrison, "Organic Chemistry," 3rd Ed, pp. 235–237 (1973).
Suzuki, Chem. Abstr. 80:133826x (1974).
Furuta, Chem. Abstr. 89:109128m (1978).
Shiozawa, Chem. Abstr. 109:128823g (1988).
Koshigoe, Chem. Abstr. 112:7918v (Jan. 1, 1990).
Sugimura, Chem. Abstr. 112:20894d (Jan. 15, 1990).

*Primary Examiner*—Michael L. Shippen
*Attorney, Agent, or Firm*—Nields & Lemack

[57] ABSTRACT

This invention relates to a process for producing an optically active cyclobutylamine which comprises reacting a racemic modification of cyclobuthylamine represented by the following general formula [I]:

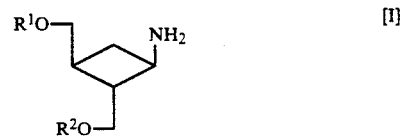

wherein $R^1$ and $R^2$ represent each a hydrogen atom or a protecting group; with an optically active N-acylphenylglycine to thereby give two corresponding diastereomeric salts, crystallizing the more difficultly soluble diastereomeric salt and isolating the corresponding optically active cyclobutylamine from the diastereomeric salt thus crystallized. The optically active substances of the compound of the above general formula [I] are useful as, for example, an intermediate in the synthesis of 9-[(1R, 2R, 3S)-2,3-bis(hydroxymethyl)-1-cyclobutyl]guanine which is expected as an antiviral agent.

5 Claims, No Drawings

PROCESS FOR PRODUCING OPTICALLY ACTIVE CYCLOBUTYLAMINES

FIELD OF THE INVENTION

This invention relates to a process for producing an optically active cyclobutylamines. It is expected that the optically active cyclobutylamine produced by the process of the present invention is usable as, for example, the starting material for producing an antiviral agent.

BACKGROUND OF THE INVENTION

Carbooxetanocins such as 9-[(1R, 2R, 3S)-2,3-bis(hydroxymethyl)-1-cyclobutyl]guanine, which are disclosed in EP-0358154-A2 and EP-0366-59-A2, are expected to be usable as antiviral agents. The aforesaid patents further disclose an optically active substances of a compound represented by the general formula [I], which will be given hereinafter, wherein $R^1$ and $R^2$ are each a silyl type protective group, as an intermediate in the synthesis of the above-mentioned compound.

It is an object of the present invention to provide a novel process for producing an optically active substances of a compound represented by the general formula [I].

SUMMARY OF THE INVENTION

The present invention relates to a process for producing an optically active cyclobutylamine which comprises reacting a racemic modification of cyclobutylamine represented by the following general formula [I]:

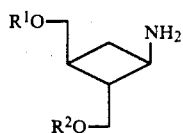

wherein $R^1$ and $R^2$ represent each a hydrogen atom or a protective group; with an optically active N-acylphenylglycine to thereby give two corresponding diastereomeric salts, crystallizing the more difficultly soluble diastereomeric salt and isolating the corresponding optically active cyclobutylamine from the diastereomeric salt thus crystallized.

DETAILED DESCRIPTION OF THE INVENTION

The protective groups represented by $R^1$ and $R^2$ in the above general formula [I] are not particularly restricted. Examples thereof include alkyl-type protective groups (for example, lower alkyl groups having one to five carbon atoms, such as methyl, ethyl, propyl and butyl groups and substituted lower alkyl groups such as a benzyl group), acyl-type protective groups for example, lower alkylcarbonyl groups such as an acetyl group (optionally having a substituent on an alkyl group), cycloalkylcarbonyl groups such as a cyclohexylcarbonyl group and arylcarbonyl groups such as a benzoyl group (optionally having a substituent on an aryl group)] and silyl-type protective groups (for example, t-butyldiphenylsilyl, t-butyldimethylsilyl and isopropyldimethylsilyl groups). Alternatively, $R^1$ and $R^2$ may be bound to each other so as to form an alkylidene group such as an alkylidene or benzylidene group, an alkyleneoxyalkylene group such as a methyleneoxymethylene group, an alkylenedicarbonyl group such as a methylenedicarbonyl group or a phosphate group.

As an example of the N-acylphenylglycine, N-acetylphenylglycine may be cited.

The process of the present invention may be effected in the following manner. In order to produce (1R, 2R, 3S)-2,3-bis(hydroxymethyl)-1-cyclobutylamine, for example, (1RS, 2RS, 3SR)-2,3-bis(hydroxymethyl)-1-cyclobutylamine is reacted with N-acetyl-L-phenylglycine in a solvent. Next, two diastereomeric salts thus formed are separated from each other by recrystallization to thereby give the more difficultly soluble (1R, 2R, 3S)-2,3-bis(hydroxymethyl)-1-cyclobutylamine/N-acetyl-L-phenylglycine salt. The solvent to be used for the recrystallization may be selected from among lower alcohols such as methanol, ethanol, propanol and isopropyl alcohol, aromatic hydrocarbons such as benzene and toluene, halogenated hydrocarbons such as dichloromethane and chloroform, alkyl acetates such as methyl acetate and ethyl acetate, ethers such as ethyl ether, dioxane and tetrahydrofuran, ketones such as acetone and 2-butanone, acetonitrile and water. From the practical viewpoint, it is preferable to use a lower alcohol having one to four carbon atoms therefor.

The reaction between the compound of the general formula [I] and the optically active N-acetylphenylglycine may be carried out by using the latter compound in an amount of 0.1 to 10 times by mol, preferably 0.5 to 2 times by mol, as much as the former and dissolving these compounds together in a solvent at a temperature of from $-20°$ C. to the boiling point of the solvent, preferably from $-20$ to $30°$ C. to thereby give 10 to 70% (w/v), preferably 20 to 50% (w/v), of diastereomeric salts.

The recrystallization may be effected in a conventional manner, for example, by lowering the concentration of the solvent, adding a solvent of a lower solubility or lowering the temperature. Examples of the solvent of a lower solubility include isopropyl alcohol, benzene, toluene and ethyl ether.

To the (1R, 2R, 3S)-2,3-bis(hydroxymethyl)-1-cyclobutylamine/N-acetyl-L-phenylglycine salt thus isolated is added an alkaline aqueous solution of, for example, sodium hydrogencarbonate, sodium carbonate or sodium hydroxide. Then the mixture is extracted with an organic solvent such as t-butanol or secbutanol. Or a solution of the salt is treated with an ion exchange resin. Then the salt is separated into the aimed free base (1R, 2R, 3S)-2,3-bis(hydromethyl)-1-cyclobutylamine and N-acetyl-L-phenylglycine. On the other hand, (1S, 2S, 3R)-2,3-bis(hydroxymethyl)-1-cyclobutylamine may be produced by the same method as the one described above except that the N-acetyl-L-phenylglycine is replaced by N-acetyl-D-phenylglycine.

Also, (1R, 2R, 3S)-2,3-bis(cyclohexylcarbonyloxymethyl)-1-cyclobutylamine is obtained using N-acetyl-D-phenylglycine by the similar method for producing (1R, 2R, 3S)-2,3-bis(hydroxymethyl)-1-cyclobutylamine as described above.

To further illustrate the present invention, the following Examples will be given.

EXAMPLE 1

Production of (1R, 2R, 3S)-2,3-bis(hydroxymethyl)-1-cyclobutylamine/N-acetyl-L-phenylglycine salt 913 mg of (1RS, 2RS, 3SR)-2,3-bis(hydroxymethyl)-1-cyclobutylamine was dissolved in 30 ml of methanol. Then 1340 mg of N-acetyl-L-phenylglycine was added thereto to form salt. The reaction mixture was concentrated under reduced pressure. 15 ml of isopropyl alcohol was added to the residue followed by fractional recrystallization. Thus 403.8 mg of (1R, 2R, 3S)-2,3-bis(hydroxymethyl)-1-cyclobutylamine/N-acetyl-L-phenylglycine salt was obtained.

$[\alpha]^{20}_D: +99.7°$ (C=1.03, MeOH)

The following compound is obtained by using N-acetyl-D-phenylglycine as resolving agent and acetone as a solvent for fractional recrystallization in the Example 1. (1R, 2R, 3S)-2,3-bis(cyclohexylcarbonyloxymethyl)1-cyclobutylamine/N-acetyl-phenylglycine salt:

$[\alpha]^{20}_D: -71.14°$ (C=1.005, MeOH)

EXAMPLE 2

Production of (1R, 2R, 3S)-2,3-bis(hydroxymethyl)-1-cyclobutylamine 309.5 mg of the (1R, 2R, 3S)-2,3-bis(hydroxymethyl)-1-cyclobutylamine/N-acetyl-L-phenylglycine salt obtained in Example 1 was treated with 50 ml of an ion exchange resin (Dowex 1-XI, a product of Muromachi Kagaku Kogyo K.K., strongly basic resin) to thereby give 121.9 mg of (1R, 2R, 3S)-2,3-bis(hydroxymethyl)-1-cyclobutylamine.

$[\alpha]^{20}_D: -21.76°$ (C=1.06, MeOH)

$^1$H-NMR (200 MHz FT, DMSO-d6) δ:
1.72 (1H, aparent q, J=9Hz)
1.86 ~2.32 (3H, m)
3,34 (1H, aparent q, J=8Hz)
3.42 (2H, d.J=5.5Hz)
3.51 (2H, brs)
4.70 (2H, brs)
7.55 (2H, brs)

Similarly, the following compound is obtained: (1R, 2R, 3S)-2,3-bis(cyclohexylcarbonyloxymethyl)-1-cyclobutylamine $[\alpha]^{20}_D: -74 85°$ (C=1.002, MeOH)

$^1$HNMR (200 MHz FF, CDCl₃) δ: 1.2 ~2.0 (24H, m) 2.31 (2H, m) 3.08 (1H, dd, J=7.6, 8.8) 4.04 (2H, dd, J=2.1, 5.3) 4.11 (2H, dd, J=2.0, 5.1)

According to the present invention, optically active (1R, 2R, 3S)-2,3-bis(hydroxymethyl)-1-cyclobutylamine can be obtained. Starting from this compound, various optically active carbocyclic oxetanocin derivatives can be obtained. For example, 9-[(1R, 2R, 3S)-2,3-bis(hydroxymethyl)-1-cyclobutyl]guanine is synthesized as follows:

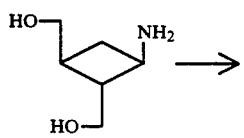

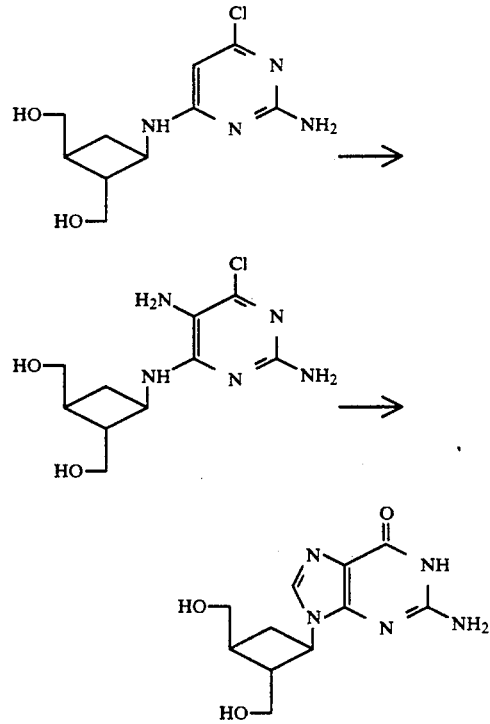

What is claimed is:

1. A process for producing an optically active cyclobutylamine which comprises reacting a racemic modification of cyclobutylamine represented by the following general formula [I]:

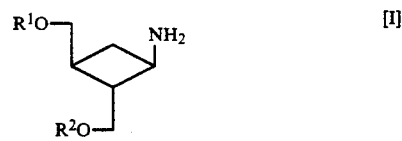

wherein $R^1$ and $R^2$ represent each a hydrogen atom or a protective group;
with an optically active N-acylphenylglycine to thereby give two corresponding diastereomeric salts, crystallizing the more difficultly soluble diastereomeric salt and isolating the corresponding optically active cyclobutylamine from the diastereomeric salt thus crystallized.

2. A process as claimed in claim 1, wherein $R^1$ and $R^2$ represent each a hydrogen atom and said optically active N-acylphenylglycine is N-acetyl-L-phenylglycine.

3. A process as claimed in claim 1, wherein $R^1$ and $R^2$ represent each a cyclohexylcarbonyl group and said optically active N-acylphenyldycine is N-acetyl-D-phenylglycine.

4. A process as claimed in claim 1, wherein said N-acylphenylglycine is used in an amount 0.1 to 10 times by mol as much as the compound of the general formula [I].

5. A process as claimed in claim 1, wherein said salts are formed in an alcoholic solvent or acetone at a temperature of from −20 ° C. to the boiling point of the solvent.

* * * * *